United States Patent
Rhodes et al.

(10) Patent No.: US 10,195,707 B2
(45) Date of Patent: Feb. 5, 2019

(54) MILLING SYSTEM

(71) Applicant: Rolls-Royce Corporation, Indianapolis, IN (US)

(72) Inventors: Jeffrey F. Rhodes, Zionsville, IN (US); Bruce Allan Crook, Mooresville, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 192 days.

(21) Appl. No.: 14/940,807

(22) Filed: Nov. 13, 2015

(65) Prior Publication Data

US 2016/0136769 A1    May 19, 2016

Related U.S. Application Data

(60) Provisional application No. 62/079,625, filed on Nov. 14, 2014.

(51) Int. Cl.
| | | |
|---|---|---|
| *B23Q 17/09* | (2006.01) | |
| *B23Q 11/10* | (2006.01) | |
| *G01N 27/20* | (2006.01) | |

(52) U.S. Cl.
CPC ...... *B23Q 17/0957* (2013.01); *B23Q 11/1038* (2013.01); *G01N 27/20* (2013.01)

(58) Field of Classification Search
CPC ............ B23Q 17/0957; B23Q 11/1038; B23B 349/001; G01N 27/20; G05B 19/4065
See application file for complete search history.

(56) References Cited

U.S. PATENT DOCUMENTS

| | | | |
|---|---|---|---|
| 3,310,796 A | 3/1967 | Sanders | |
| 3,339,434 A * | 9/1967 | Sparling | ............... B23B 49/001 |
| | | | 324/166 |
| 3,584,522 A | 6/1971 | Smafield | |
| 3,747,085 A | 7/1973 | Bala et al. | |
| 3,912,925 A | 10/1975 | Gaskell | |
| 3,990,805 A | 11/1976 | Ducrohet | |
| 4,340,326 A | 7/1982 | Buonauro et al. | |
| 4,502,823 A | 3/1985 | Wronski et al. | |
| 4,604,006 A | 8/1986 | Shoji et al. | |
| 4,667,113 A | 5/1987 | Nakajima et al. | |
| 4,694,686 A * | 9/1987 | Fildes | ................. G05B 19/4065 |
| | | | 324/71.1 |

(Continued)

FOREIGN PATENT DOCUMENTS

| | | | | |
|---|---|---|---|---|
| DE | 102014204833 A1 * | 9/2015 | ........... | B23Q 17/957 |
| EP | 2165803 A1 * | 3/2010 | ......... | B23Q 17/0909 |

*Primary Examiner* — Alan Snyder
(74) *Attorney, Agent, or Firm* — Shumaker & Sieffert, P.A.

(57) ABSTRACT

In one example, a method including controlling milling of a component via a milling system, the milling system including a spindle, a tool holder coupled to the spindle, the tool holder configured to receive a milling tool; and the milling tool configured to remove at least a portion of the component via milling while the milling tool is rotated by the spindle and tool holder, wherein the milling system is configured to conduct an electrical signal between the milling tool and component during milling of the component when the milling tool is not broken; monitoring the electrical signal conducted between the milling tool and component; and determining whether the milling tool is broken based on the monitored electrical signal.

19 Claims, 6 Drawing Sheets

(56) References Cited

U.S. PATENT DOCUMENTS

| | | | |
|---|---|---|---|
| 4,718,175 A | | 1/1988 | Babel |
| 4,786,220 A | * | 11/1988 | Fildes .................... G01N 3/56 408/11 |
| 4,850,754 A | | 7/1989 | Thornton et al. |
| 5,090,847 A | | 2/1992 | Gelston, II |
| 5,096,339 A | | 3/1992 | Shoji |
| 5,189,625 A | | 2/1993 | Le Floch |
| 5,293,048 A | | 3/1994 | Skunes et al. |
| 5,404,021 A | | 4/1995 | Mangano et al. |
| 5,584,216 A | * | 12/1996 | Sinjen .................... B21D 28/34 83/62.1 |
| 5,599,142 A | | 2/1997 | Fujimoto et al. |
| 7,403,868 B2 | | 7/2008 | Maekawa et al. |
| 2012/0182029 A1 | * | 7/2012 | Lange .................... B23Q 17/09 324/691 |

* cited by examiner

MILLING SYSTEM

This application claims the benefit of U.S. Provisional Application No. 62/079,625, by Rhodes et al., and filed Nov. 14, 2014, the entire content of which is incorporated herein by reference.

TECHNICAL FIELD

This disclosure generally relates to milling systems and techniques, and more particularly, but not exclusively, to automated milling systems and techniques.

BACKGROUND

Various systems and techniques exist for milling components having complex shapes and surfaces that are susceptible to geometric variations, such as blades and vanes of gas turbine engines. Some existing systems and techniques have various shortcomings, drawbacks, and disadvantages relative to certain applications. Accordingly, there remains a need for further contributions in this area of technology.

SUMMARY

This disclosure describes, in some examples, milling techniques as well as apparatuses, systems, devices, hardware and combinations, e.g., for automated milling of components. An automated milling system may include a tool holder coupled to a spindle. The tool holder may secure a milling tool, which is rotated by the spindle when the tip of the milling tool is in contact with a component to remove selected portions of the component. During the milling process, the milling system may control, e.g., via computer numerical control (CNC), the movement of the milling tool relative the milled component to provide the component with a desired 3-dimensional surface geometry.

An automatic milling system may be configured such that, during milling of a component, an electrical signal is conducted between the milled component and milling tool when the tool is in contact with the component. In the event that the milling tool breaks during milling, the electrical signal may no longer be conducted between the milled component and milling tool, e.g., since the milling tool is no longer is electrical contact with the component. The milling system may be configured, e.g., via one or more processors, to monitor the electrical signal and detect when the milling tool breaks during milling based on the monitored electrical signal. In this manner, the milling system may suspend milling operation when it is determined that the milling tool is broken to replace the milling tool or otherwise remedy the broken milling tool.

In one example, this disclosure is directed to a method comprising controlling milling of a component via a milling system, the milling system including a spindle; a tool holder coupled to the spindle, the tool holder configured to receive a milling tool; and the milling tool configured to remove at least a portion of the component via milling while the milling tool is rotated by the spindle and tool holder, wherein the milling system is configured to conduct an electrical signal between the milling tool and component during milling of the component when the milling tool is not broken; monitoring the electrical signal conducted between the milling tool and component; and determining whether the milling tool is broken based on the monitored electrical signal, wherein at least one of the controlling, monitoring, or determining is performed via at least one processor.

In another example, this disclosure is directed to an automated milling system comprising a spindle; a tool holder coupled to the spindle, the tool holder configured to receive a milling tool; the milling tool configured to remove at least a portion of the component via milling while the milling tool is rotated by the spindle and tool holder, wherein the milling system is configured to conduct an electrical signal between the milling tool and component during milling of the component when the milling tool is not broken; and a processor configured to monitor an electrical signal conducted between the milling tool and component, and determined whether the milling tool is broken based on the monitored electrical signal.

In another example, this disclosure is directed to an non-transitory computer readable storage medium including instructions that cause one of more processors to control milling of a component via a milling system, the milling system including a spindle; a tool holder coupled to the spindle, the tool holder configured to receive a milling tool; and the milling tool configured to remove at least a portion of the component via milling while the milling tool is rotated by the spindle and tool holder, wherein the milling system is configured to conduct an electrical signal between the milling tool and component during milling of the component when the milling tool is not broken; monitor the electrical signal conducted between the milling tool and component; and determine whether the milling tool is broken based on the monitored electrical signal.

The details of one or more examples of this disclosure are set forth in the accompanying drawings and the description below. Other features, objects, and advantages of this disclosure will be apparent from the description and drawings.

DETAILED DESCRIPTION

For the purposes of promoting an understanding of the principles of the disclosure, reference will now be made to the examples illustrated in the drawings and specific language will be used to describe the same. It will nevertheless be understood that no limitation of the scope of the disclosure is thereby intended. Any alterations and further modifications in the described examples, and any further applications of the principles of the disclosure as described herein are contemplated as would normally occur to one skilled in the art to which the disclosure relates.

As described above, some examples of the disclosure relate to automated milling systems, e.g., used to mill components of a gas turbine engine. An automated milling system may include a tool holder coupled to a spindle. The tool holder may secure a milling tool, which is rotated by the spindle when the tip of the milling tool is in contact with a component to remove selected portions of the component. During the milling process, the milling system may control, e.g., CNC, the movement of the milling tool relative the milled component to provide the component with a desired 3-dimensional surface geometry.

In some examples, milling tools may break during milling of a component e.g., due to stress and other forces applied to the tool during the milling process. Various example techniques may be used to detect breakage of a milling tool. In one example, the milling process is temporarily stopped and the milling tool is inspected for breakage using suitable techniques. However, such a process delays the milling process unnecessarily in times that the milling tool is found to be intact. Further, the milling process may continue for some period of time after brakeage of the milling tool before the break is detected.

In other examples, techniques for detection milling tool breakage in real time during the milling process may be utilized. For example, milling tool breakage techniques involving the monitoring of spindle horsepower, cutting acoustics, and/or dynamic displacement of the work piece may be employed. However, such techniques may not adequately detect the breakage of milling tool, particularly in the case of relatively small milling tools, e.g., milling tools with a diameter of about 30 mils or less.

In accordance with one or more examples of the disclosure, milling systems and techniques are described which may be employed to detect breakage of milling tools, including in real time during milling of a component. Examples include milling systems which are configured such that an electrical signal is transmitted between the milling tool and component being milled during the milling process. In particular, the electrical signal may be transmitted between the milling tool and the component being milled when the milling tool is in contact with the component. If the milling tool breaks during milling, the milling tool may lose contact with the component, thus not allowing for the electrical signal to be transmitted between the milling tool and component. In such cases, the milling system may include a processor configured to monitor the electrical signal and detect breakage of the milling tool based on the electrical signal, e.g., based on whether or not the electrical signal is being transmitted between the milling tool and milled component. Various milling system configurations may be employed to allow for a processor to determine whether or not an electrical signal is being transmitted between the milling tool and milled component, including those configurations described with regard to FIGS. 3-6.

Figure 1:
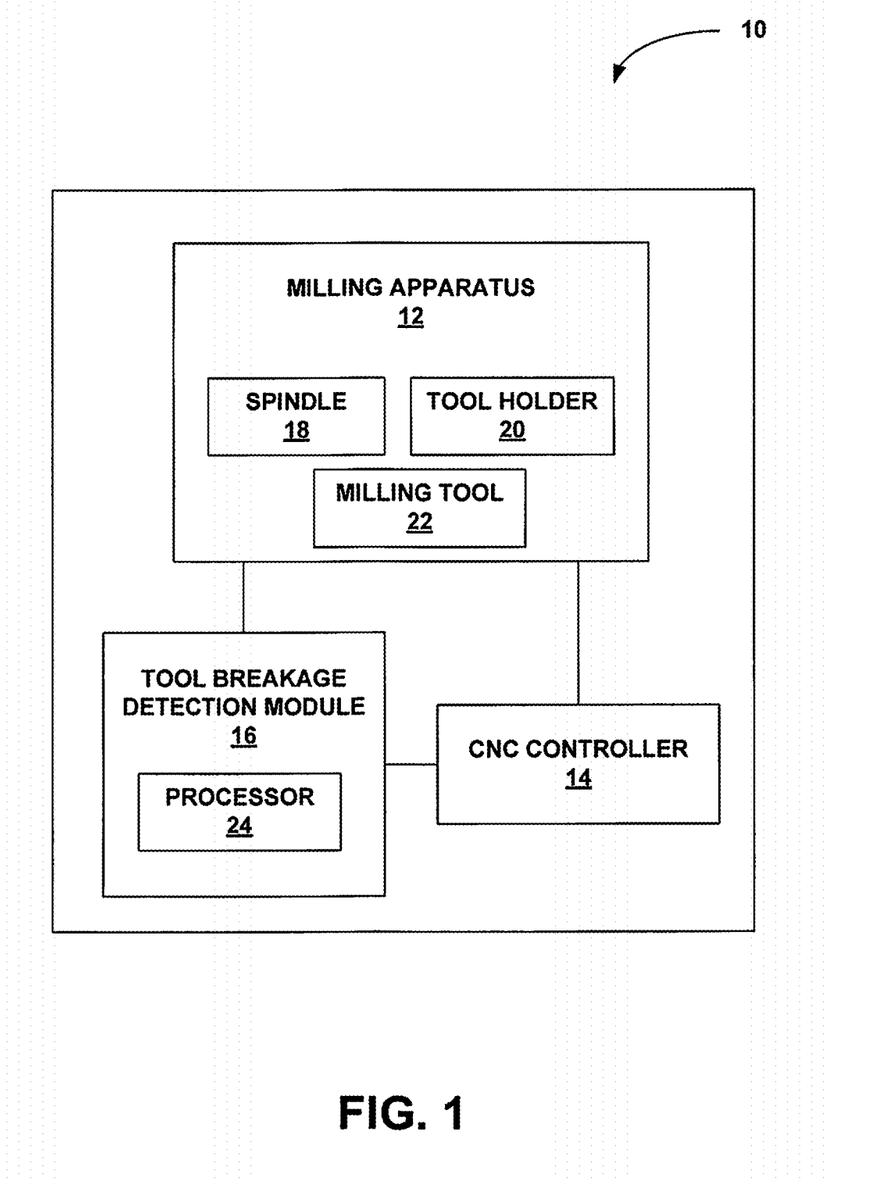
FIG. 1 is a functional schematic diagram illustrating an example automated milling system.

FIG. 1 is a functional diagram illustrating an example automated milling system 10. Automated milling system 10 of the FIG. 1 is described in the context of milling a component of a gas turbine engine. However, it will be understood by those of ordinary skill in the art that automated milling system 10 is not limited in application to gas turbine engine components, and other example applications are contemplated. A few non-limiting examples to which automated milling system 10 can be applied include components in the aerospace industry, such as landing gear components or wing and fuselage components; the turbomachinery industry, such as turbine components and compressor components; the automobile industry, such as press tools for body panels; and other manufacturing industries. In some examples, automated milling system 10 can be applied to the repair of components, for example the repair of gas turbine engine blades and/or vanes.

In the example illustrated in FIG. 1, milling system 10 includes milling apparatus 12, CNC controller 14, and tool breakage detection module 16. Milling apparatus 12 includes spindle 18, tool holder 20, and milling tool 22. CNC controller 20 may control operation of milling apparatus 12 to mill a component (not shown) via milling tool 22. For example, during milling, CNC controller 14 may control the motor (not shown) which drives the rotation of spindle 18 and, thus, milling tool 22. CNC controller 14 may also control the position of milling tool 22 relative the component surface being milled, e.g., by moving the milling tool 22 and/or the component being milled. CNC controller 14 may perform such functions to provide for a milled component having a desired surface or 3-D geometry.

In some examples, CNC controller 14 may include a microprocessor or multiple microprocessors capable of executing and/or outputting command signals in response to received and/or stored data. CNC controller 14 may include computer-readable storage, such as read-only memories (ROM), random-access memories (RAM), and/or flash memories, or any other components for running an application and processing data for controlling operations associated with automated milling system 10. Thus, in some examples, CNC controller 14 may include instructions and/ or data stored as hardware, software, and/or firmware within the one or more memories, storage devices, and/or microprocessors. In some examples, CNC controller 14 may include and/or be associated with surface modeling circuitry, regression analysis circuitry, program code modification circuitry, switches, and/or other types of circuitry, as suited for an automated milling application. CNC controller 14 may include multiple controllers or only a single controller.

Milling tool 12, which may also be referred to as a milling cutter, may take any suitable geometrical form configured to mill or otherwise remove portion of the milled component when rotated via spindle 18 in contact with the surface component being milled. For relatively fine milling operations, milling tool 12 may have relatively small dimensions. For example, milling tool 12 may have a diameter at the distal portion (i.e., end portion that contacts surface of the milled component) of approximately 30 mils or less. Milling tool 12 may be removably coupled to spindle 18 via tool holder 20. Such an orientation allows for milling tool 12 to be replaced if needed, e.g., to employ a milling tool with a different shape or if milling tool 12 breaks during the milling process.

As noted above, system 10 may be used to form a desired 3-D surface geometry in a milled component by selectively removing portions of the component via milling. Example substrate compositions include ceramic matrix composite substrates, superalloy substrate, and other materials used, e.g., in the aerospace industry. In some examples, the substrate may be formed of an electrically conductive material, while others examples the substrate may be formed of a relatively high electrically resistant material. However, milled components may be formed of materials other than those mentioned above.

During the milling process, milling tool 12 may break, e.g., due to stress and other forces applied to the tool during the milling process. As shown in FIG. 1, milling system 10 includes tool breakage detection module 16. As will be described further below, tool breakage detection module 16 may be configured to detect when milling tool 12 breaks, e.g., in real-time during milling operation. In particular, processor 24 of tool breakage detection module 16 may monitor (continuous or periodically) an electrical signal conducted between milling tool 22 and the component being milled via milling tool 22. Based on the changes in the monitored signal when the milling tool 22 is intact and, thus, the electrical signal is being conducted with the milled component versus when milling tool 22 is broken and, thus, no electrical signal is being conducted with the milled component, processor 24 may detect whether or not milling tool 22 is broken.

Processor 24 may include any one or more microprocessors, controllers, digital signal processors (DSPs), application specific integrated circuits (ASICs), field-programmable gate arrays (FPGAs), and discrete logic circuitry. The functions attributed to processors and tool breakage detection module 16 described herein, including processor 24, may be provided by a hardware device and embodied as software, firmware, hardware, or any combination thereof. Although not shown, tool breakage detection module 16 may also include a memory, which may include any volatile or non-volatile media, such as a random access memory (RAM), read only memory (ROM), non-volatile RAM (NVRAM), electrically erasable programmable ROM (EE-PROM), flash memory, and the like. The memory may store computer-readable instructions that, when executed by processor 24, cause system 10 to perform various functions described herein. The memory may be considered, in some examples, a non-transitory computer-readable storage medium comprising instructions that cause one or more processors, such as, e.g., processor 24, to implement one or more of the example techniques described in this disclosure. The term "non-transitory" may indicate that the storage medium is not embodied in a carrier wave or a propagated signal. However, the term "non-transitory" should not be interpreted to mean that the memory is non-movable. In certain examples, a non-transitory storage medium may store data that can, over time, change (e.g., in RAM).

Figure 2:
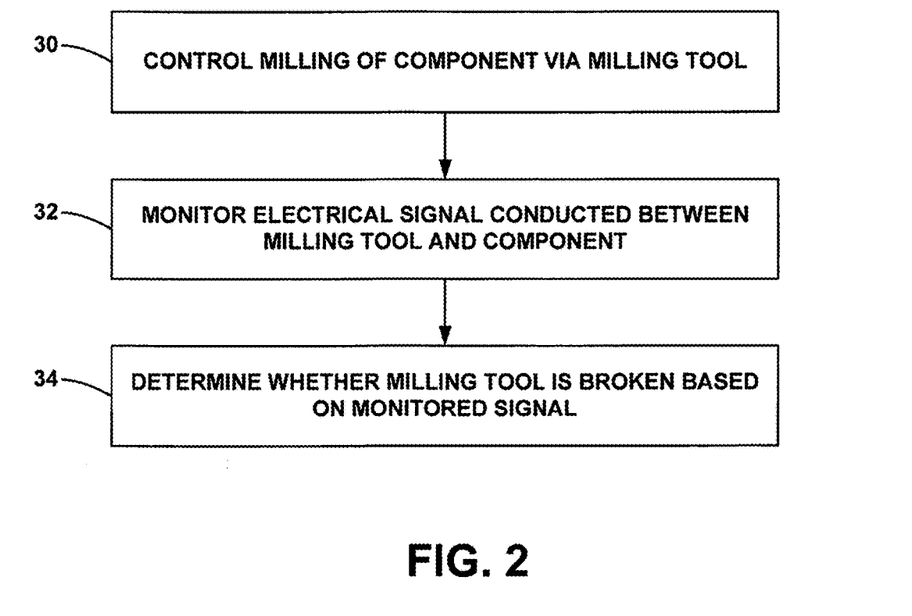
FIG. 2 is a flow diagram illustrating an example automated milling technique.

FIG. 2 is a flow chart illustrating an example technique performed by an automated milling system to detect milling tool breakage, e.g., while milling a component. For ease of illustration, the example technique of FIG. 2 is described with regard to milling system 10. However, any suitable milling systems may employ the technique of FIG. 2 to detect milling tool breakage.

As shown in FIG. 2, CNC controller 14 may control milling apparatus 12 to mill portions of a component, e.g., in the manner described above (30). System 10 may be configured such that an electrical signal is conducted between milling tool 22 and the component being milled when milling tool 22 is intact. Processor 24 of tool breakage detection module 16 may monitor this electrical signal (32), and determine whether or not the milling tool 22 is broken or intact based on the monitored signal (34). As noted above, processor 24 may monitor the electrical signal on a substantially continuous basis or periodically sample the electrical signal (32). As one or more characteristics of the monitored signal may change based on whether or not milling tool 22 is broken, processor 24 may detect whether tool 22 is broken or not based on analysis of such a characteristic in the monitored signal. In some examples, tool breakage detection module 24 may include one or more suitable analog to digital convertors and comparator logic to allow processor 24 to analyze the monitored signal, e.g., in terms of voltage, and determine whether the monitored signal indicates that milling tool 22 is broken.

In one example, processor 24 may compare one or more parameters of the signal (e.g., voltage) to a predetermined threshold for the parameter to detect breakage of milling tool 22. For example, the predetermined threshold determined for the signal parameter may correspond to a threshold indicative of milling too 22 being broken, e.g., a value of the parameter at or below the threshold may be indicative of milling tool 22 not being broken while a value above the threshold may be indicative of milling tool 22 being broken. Other suitable techniques may also be used.

In the example of FIG. 2, processor 24 may monitor the electrical signal during milling operation, e.g., while spindle 18 is rotating milling tool 22 to remove portions of the milled component, to allow for real-time detection of breakage of milling tool 22 during milling (34). Additionally or alternatively, CNC controller 14 may periodically suspend milling operation, during which time processor 22 determines whether or not the electrical signal characteristics indicate that milling tool 22 is broken (34).

If processor 24 determines that the monitored electrical signal indicates that milling tool 22 is broken, processor 24 may generate an indication to CNC controller that such a determination has been made. In response, CNC controller 14 may suspend the milling operation, e.g., by suspending the rotation of spindle 18. When suspended, milling tool 22 may be replaced with another intact tool, e.g., by removing milling tool 22 from tool holder 20 and coupling a replacement tool to tool holder 20. In some examples, prior to replacement, one or more other techniques may be used to further determine whether or not milling tool 22 is indeed broken, or if the determination made by tool breakage detection module was incorrect.

Any suitable milling system configuration may be employed to perform one or more of the example techniques described herein. FIGS. 3-6 are functional schematic diagram illustrating various example automated milling system which may be configured to detect milling tool breakage, e.g., using the example technique of FIG. 2. Each of the systems shown in FIGS. 3-6 may be an example in accordance with milling system 10 of FIG. 1. Like components and features are similarly numbered throughout the figures.

FIGS. 3-6 include a representation of the electrical circuit by which tool breakage detection module 16 may detect whether or not milling tool 22 is broken. As will be apparent from the description below, each of the example milling systems in FIGS. 3-6, tool breakage detection module 16 is configured to detection breakage of milling tool 22 by determining whether or not a voltage is detected during milling of a component. In particular, each example milling system is configured such that substantially no voltage will be detected by tool breakage detection module 16 when an electrical signal is conducted between milling tool 22 and the milled component. Conversely, when milling tool 22 breaks and, thus, substantially no electrical signal is conducted between milling tool 22 and the milled component, tool breakage detection module 16 detects a voltage. Based on the detected voltage, tool breakage detection module 16 determines that milling tool 22 is broken.

Figure 3:
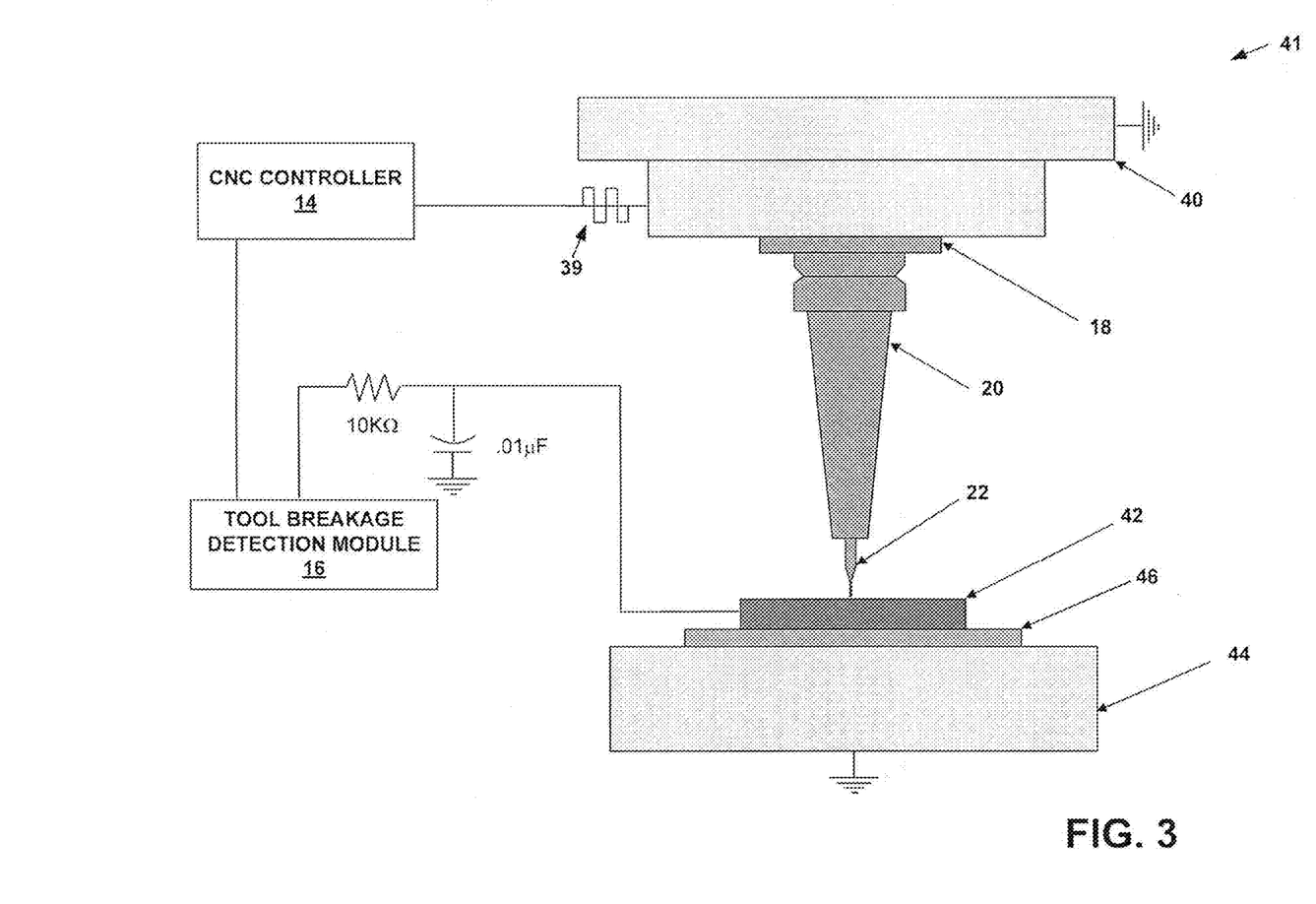
FIGS. 3-6 are functional schematic diagrams illustrating various example automated milling systems.

FIG. 3 is a functional schematic diagram illustrating example automated milling system 41. As shown, system 41 includes spindle housing 40, which houses the internal components of spindle 18 which allow spindle to be rotated, e.g., via motor controller by CNC controller 14. Milled component 42 is secured to machine table 44 during the milling operation. Milling table 44 is electrically grounded and electrical insulator 46 separates component 42 from milling table 44 to substantially electrically isolate component 42 from milling table 44. Spindle housing 40 is also electrically grounded but the spindle is ungrounded.

To remove portions of component 42, CNC controller 14 controls a motor to rotate spindle 18, thus rotating milling tool 42. While rotating, CNC controller 14 brings milling tool 22 into contact with the surface of milled component 42 at a desired location to selectively remove a portion of milled component 42. The milling process is carried out until portions of milled component have been removed to provide a component with a desired surface geometry.

In some examples, the motor driving the rotation of spindle 18 may generate an electromotive force (EMF) while rotating spindle 18, represented in FIG. 3 by waveform 39, going to the ground. For example, an asynchronous induction motor may generate such an EMF with sufficient potential to allow for monitoring of the electrical signal via the example technique of FIG. 3. In some examples, the EMF potential peak to peak may be approximately 10 volts. The configuration of system 41 allows for the transmission of this electrical signal between milling tool 22 and milled component 42.

Tool breakage detection module is electrically couple to milled component 42, e.g., using suitable electrical coupling components. As noted above, while milling tool 22 is intact, tool detection breakage module 16 may detect substantially no voltage. Conversely, when milling tool 22 is broken and not in contact with milled component 42, tool detection breakage module 16 may detect a voltage. Based on the detected voltage, tool detection breakage module 16 may detect that milling tool 22 is broken and transmit an indication to CNC controller 14 indicating a breakage of milling tool 22. Based on this indication, CNC controller 14 may suspend milling, e.g., by stopping rotation of spindle 18, to allow for inspection and/or replacement of milling tool 22.

The configuration of system 41 may be particularly desirable in cases in which spindle 18 is ungrounded and a non-conductive coolant is employed during the milling process to cool milled component 42 and milling tool 22, e.g., by flooding or misting the coolant during the milling process. Example non-conductive coolants include mineral oil and vegetable oil. In some examples, the non-conductive coolant may exhibit a resistance of more than approximately 10,000,000 ohms or conductivity less than approximately 0.0000001 siemens.

However, in cases in which a conductive coolant, such as, e.g., a water-based synthetic coolant, is employed, the conductive coolant may cause the voltage of EMF from the motor to drop to a level that is not suitable for monitoring by tool detection breakage module 16 according to the example technique of FIG. 2. In some examples, the conductive coolant may exhibit a resistance of less than approximately 10,000,000 ohms or conductivity more than approximately 0.0000001 siemens.

Figure 4:
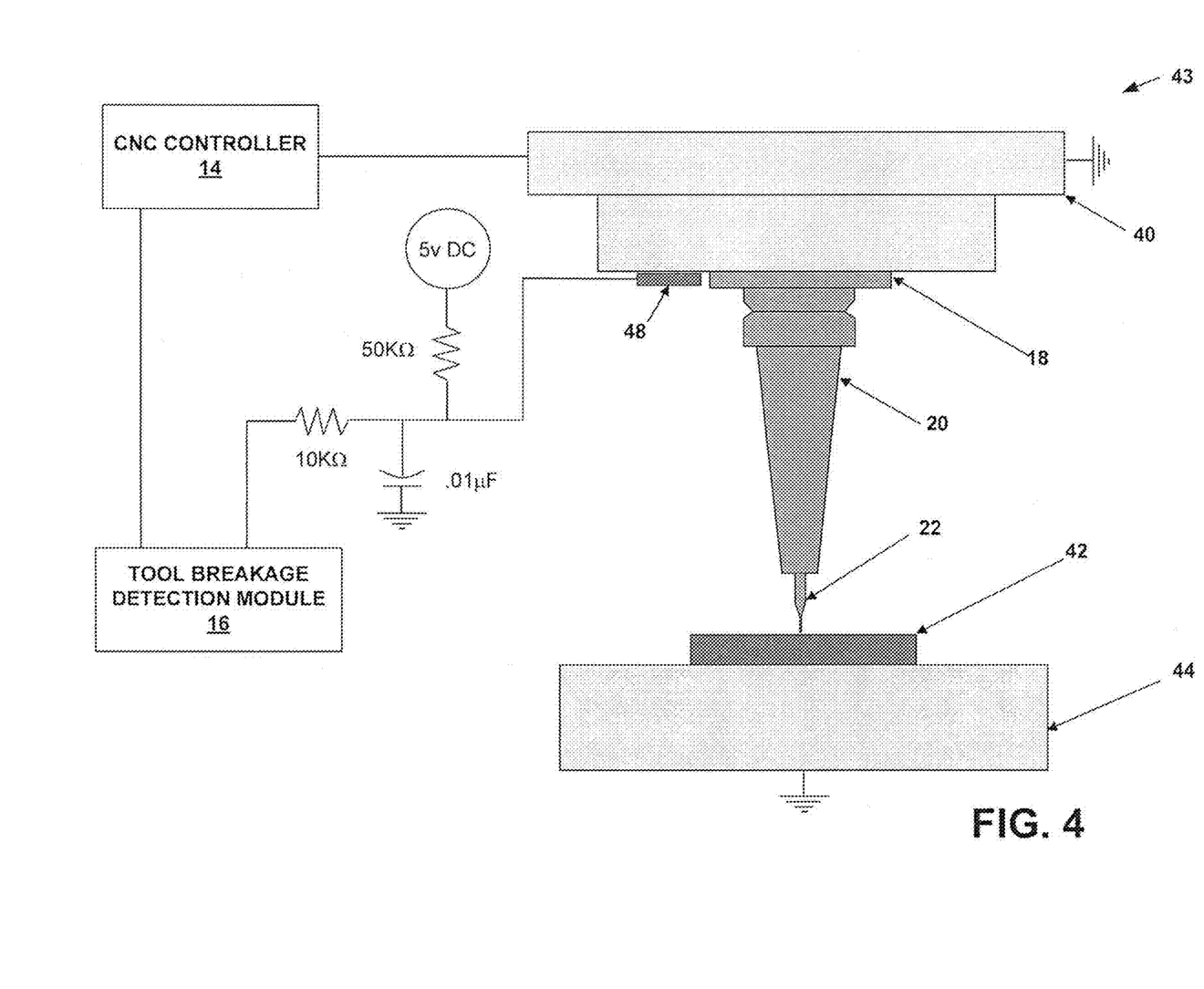
Figure 5:
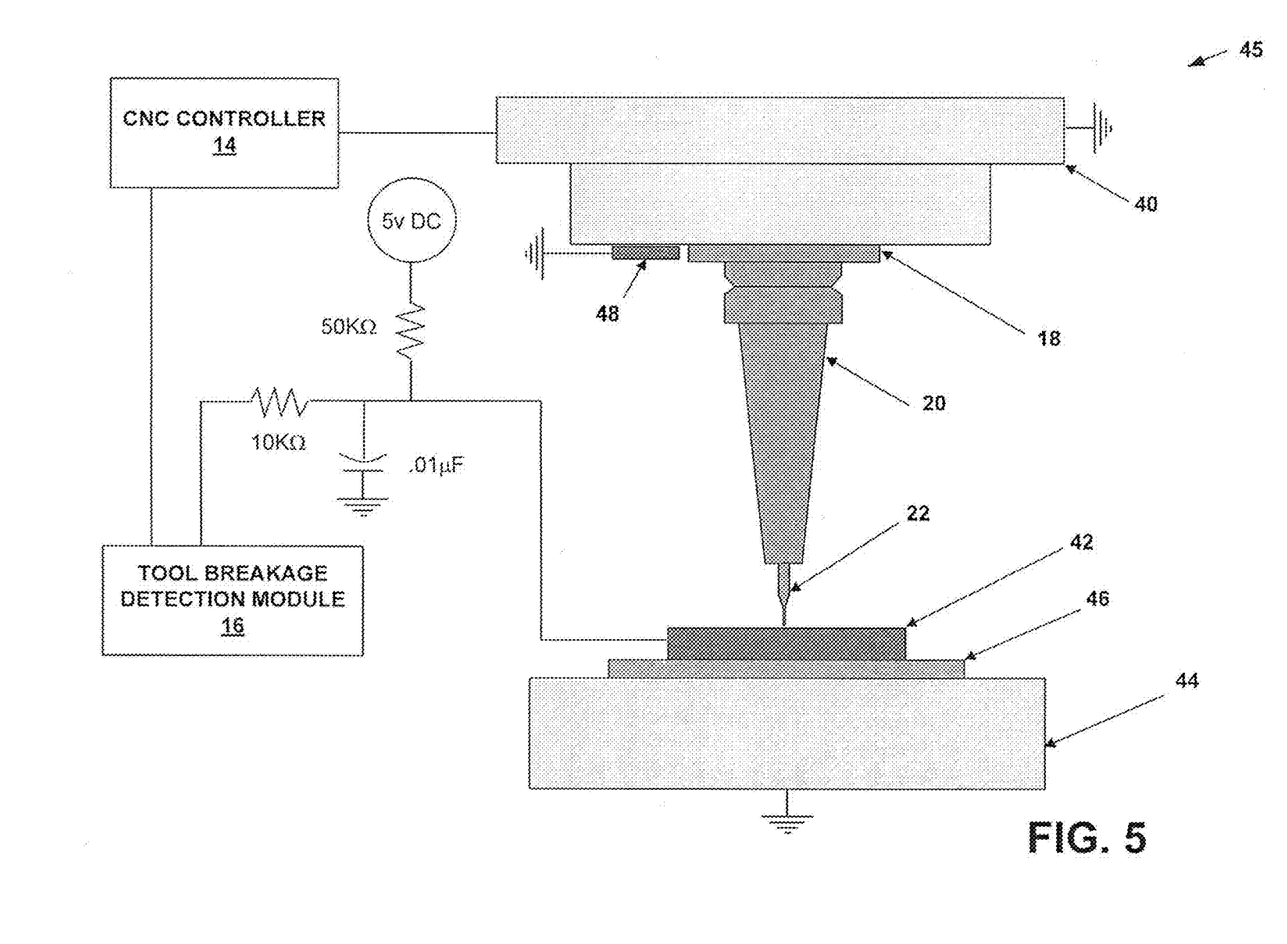

FIGS. 4 and 5 illustrate example milling system configurations which may be employed for detecting milling tool breakage, e.g., when a conductive coolant is employed. In FIG. 4, the configuration includes an ungrounded spindle. FIG. 4 is a functional schematic diagram illustrating example automated milling system 43. Machine table 44 and spindle housing 40 are grounded and spindle 22 is ungrounded in system 43. FIG. 5 is a functional schematic diagram illustrating another example automated milling system 45. In system 45, machine table 44 and spindle housing 40 are grounded. Similarly, spindle 18 is grounded through slip ring 48 in system 43. System 45 of FIG. 5 also includes electrical insulator 46 that separates component 42 from milling table 44 to substantially electrically isolate component 42 from milling table 44, similar to that of system 41.

As shown in FIGS. 4 and 5, both systems 43 and 45 include conductive slip ring 48 positioned on spindle housing 40 proximate to spindle 18. Conductive slip ring 48 is not in direct physical contact with spindle 18 but instead is separated from the surface of spindle 18 by a small gap. As such, spindle 18 is allowed to rotate freely with being impeded by slip ring 18. Conductive slip ring 48 may be formed of a conductive material to form an electrode. Due to the close proximity of conductive slip ring 48 to spindle 18, an electric signal may be conducted between conductive slip ring 48 and spindle 18, particularly in the presence of a conductive coolant during milling if component 42. In some examples, conductive slip ring 48 may be separated from spindle 18 by a gap on the order of mils, such as, e.g., between about 1 mils and about 50 mils, between about 1 mils and about 30 mils, between about 1 mils and about 20 mils, or between about 5 mils and about 30 mils.

Regardless of the particular distance separating conductive slip ring 48 and spindle 18, the separation is such that an electrical signal may be conducted between spindle 18 and slip ring 48, e.g., in the presence of the conductive coolant being employed in the milling process. In each of systems 43 and 45, a direct current is conducted through a circuit in a manner that allows for tool breakage detection module 16 to determine whether or not milling tool 22 is broken by monitoring the electrical signal. The configuration in which an electrical signal to be conducted between conductive slip ring 48 and spindle 18 completes the electrical circuit indicated in each of system 43 and 45, thus allowing tool breakage detection module 16 to monitor for milling tool breakage in the manner described herein.

For example, in system 43 of FIG. 4, milled component 42 is ground with milling table 44 and the conducted signal is pulled off conductive slip ring 48 from spindle 18. Conversely, in system 45 of FIG. 5, milled component 42 is not grounded due to electrical insulator 46 separating component 42 from grounded milling table 44. Instead, conductive slip ring 48 is grounded to ground spindle 18. In such a configuration, the conducted signal is pulled off milled component 42. The path to complete the circuit is through a resister of the 5 volt power source.

However, in each of system 43 and 45, the circuit allows for tool breakage detection module 16 to monitor the electrical signal conducted, e.g., during milling of component 42, as described herein to detect breakage of milling tool 22. For example, as noted above, while milling tool 22 is intact, tool detection breakage module 16 may detect substantially no voltage. Conversely, when milling tool 22 is broken and not in contact with milled component 42, tool detection breakage module 16 may detect a voltage. Based on the detected voltage, tool detection breakage module 16 may detect that milling tool 22 is broken and transmit an indication to CNC controller 14 indicating a breakage of milling tool 22. Based on this indication, CNC controller 14 may suspend milling, e.g., by stopping rotation of spindle 18, to allow for inspection and/or replacement of milling tool 22.

Figure 6:
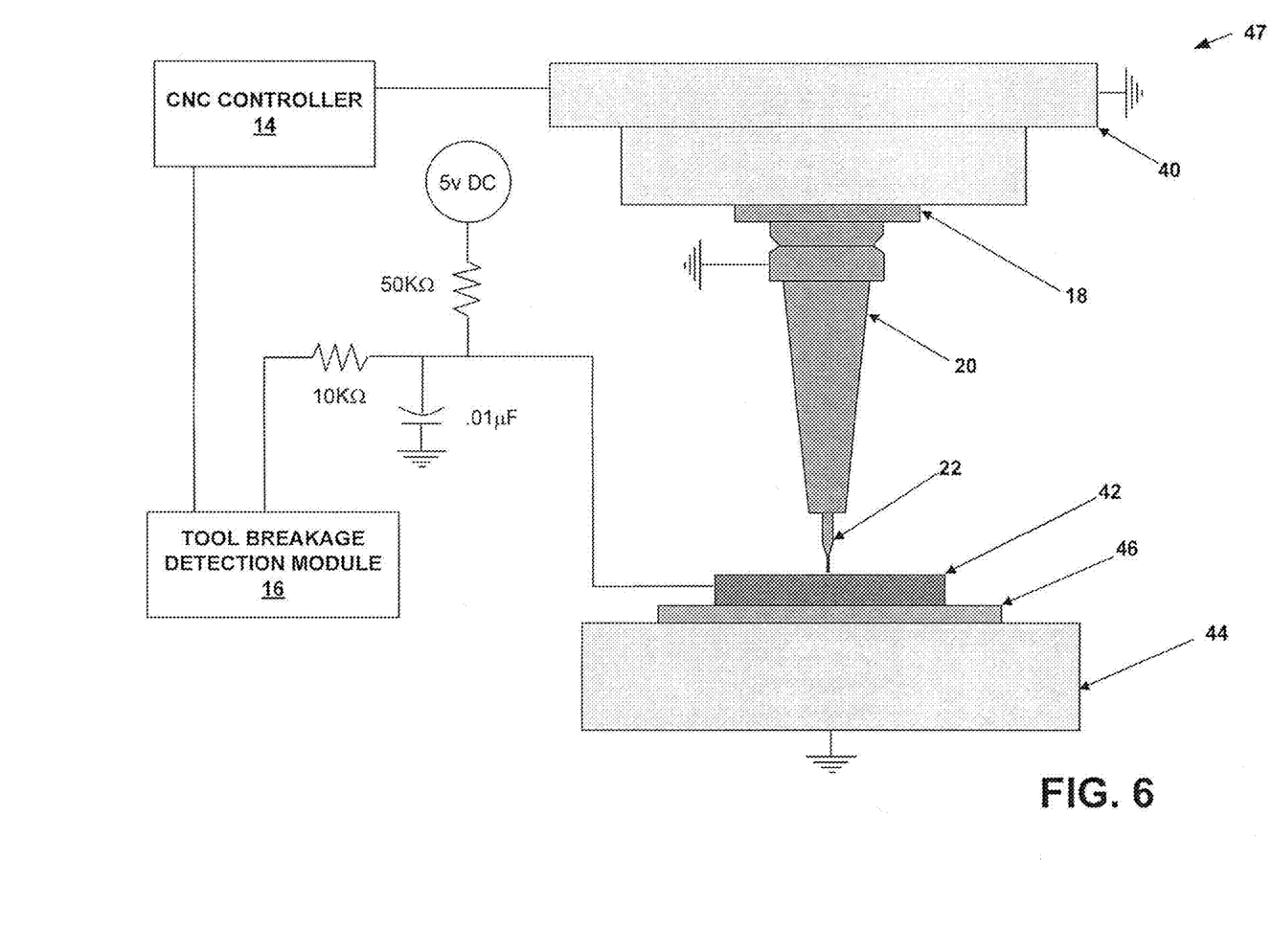

FIG. 6 is a functional schematic diagram illustrating another example automated milling system 47. As shown in FIG. 6, machine table 44 and spindle housing 40 are grounded. System 47 of FIG. 5 also includes electrical insulator 46 that separates component 42 from milling table 44 to substantially electrically isolate component 42 from milling table 44, similar to that of system 41. As such, system 47 is similar to that of system 45 in FIG. 5 and allows for tool breakage detection module 16 to monitor for tool breakage in a manner similar to that described for system 45. However, while spindle 22 is grounded in both configurations, in system 47, spindle 22 is grounded without the use of grounded slip ring 48.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the one or more processors. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media.

Various examples have been described. These and other examples are within the scope of the following claims.

What is claimed is:

1. A method comprising:
controlling milling of a component via a milling system, the milling system including:
a spindle;
a tool holder coupled to the spindle, the tool holder configured to receive a milling tool; and
the milling tool configured to remove at least a portion of the component via milling while the milling tool is rotated by the spindle and tool holder, wherein the milling system is configured to conduct an electrical signal between the milling tool and component during milling of the component when the milling tool is not broken;
monitoring the electrical signal conducted between the milling tool and component; and
determining whether the milling tool is broken based on a detected voltage of the monitored electrical signal, wherein determining whether the milling tool is broken based on the detected voltage of the monitored electrical signal comprises:
determining the milling tool is not broken when substantially no voltage is detected; and
determining the milling tool is broken when a voltage is detected,
wherein at least one of the controlling, monitoring, or determining is performed via at least one processor.

2. The method of claim 1, wherein monitoring the electrical signal conducted between the milling tool and component comprises monitoring the electrical signal conducted between the milling tool and component during milling of the component.

3. The method of claim 1, further comprising suspending the milling of the component based on the determination that the milling tool is broken.

4. The method of claim 1, wherein the milling system includes an electrically conductive slip ring proximate the spindle with a gap between the spindle and slip ring, wherein the electrical signal is conducted between the slip ring and spindle across the gap.

5. The method of claim 4, wherein an electrically conductive coolant cools the milling tool during the milling of the component.

6. The method of claim 4, wherein the slip ring is grounded.

7. The method of claim 5, wherein at least one of the spindle, the component, or the slip ring is grounded.

8. The method of claim 1, wherein the spindle is not grounded.

9. The method of claim 1, wherein an electrically non-conductive coolant cools the milling tool during the milling of the component, and wherein the spindle and the component are ungrounded.

10. An automated milling system comprising:
a spindle;
a tool holder coupled to the spindle, the tool holder configured to receive a milling tool;
the milling tool configured to remove at least a portion of the component via milling while the milling tool is rotated by the spindle and tool holder, wherein the milling system is configured to conduct an electrical signal between the milling tool and component during milling of the component when the milling tool is not broken; and
a processor configured to monitor an electrical signal conducted between the milling tool and component, and determine whether the milling tool is broken based on a detected voltage of the monitored electrical signal, wherein the processor determines that the milling tool is not broken when no voltage is detected and the processor determines that the milling tool is broken when a voltage is detected.

11. The system of claim 10, wherein the processor is configured to monitor the electrical signal conducted between the milling tool and component during milling of the component.

12. The system of claim 10, wherein the processor is configured to suspend the milling of the component based on the determination that the milling tool is broken.

13. The system of claim 10, further comprising an electrically conductive slip ring proximate the spindle with a gap between the spindle and slip ring, wherein the gap is configured such that the electrical signal is conducted between the slip ring and spindle across the gap.

14. The system of claim 13, wherein the system is configured such that a conductive coolant cools the milling tool during the milling of the component.

15. The system of claim 14, wherein at least one of the spindle, the component, or the slip ring is grounded.

16. The system of claim 13, wherein the slip ring is grounded.

17. The system of claim 10, wherein the spindle is not grounded.

18. The system of claim 10, wherein the system is configured such that a non-conductive coolant cools the milling tool during the milling of the component, and wherein the spindle and the component are ungrounded.

19. A non-transitory computer readable storage medium including instructions that cause one or more processors to:
control milling of a component via a milling system, the milling system including:
a spindle;
tool holder coupled to the spindle, the tool holder configured to receive a milling tool; and
the milling tool configured to remove at least a portion of the component via milling while the milling tool is rotated by the spindle and tool holder, wherein the milling system is configured to conduct an electrical signal between the milling tool and component during milling of the component when the milling tool is not broken;
monitor the electrical signal conducted between the milling tool and the component; and
determine whether the milling tool is broken based on a detected voltage of the monitored electrical signal, wherein the milling tool is determined to be not broken when substantially no voltage is detected and the milling tool is determined to be broken when a voltage is detected.

* * * * *